(12) United States Patent
Keller et al.

(10) Patent No.: US 6,168,630 B1
(45) Date of Patent: Jan. 2, 2001

(54) HAND JOINT PROSTHESIS (75) Inventors: Arnold Keller, Kayhude; Heiner Thabe, Bad Kreuznach, both of (DE)

(73) Assignee: Waldemar Link (GmbH & Co), Hamburg (DE)

( * ) Notice: Under 35 U.S.C. 154(b), the term of this patent shall be extended for 0 days.

(21) Appl. No.: 09/253,114

(22) Filed: Feb. 19, 1999

(51) Int. Cl.[7] .................................................. A61F 2/42
(52) U.S. Cl. .................................. 623/21.11; 623/21.12
(58) Field of Search ........................... 623/21, 20, 18.11, 623/21.11, 21.12

(56) References Cited

U.S. PATENT DOCUMENTS

| | | | |
|---|---|---|---|
| 4,259,752 | * | 4/1981 | Taleisnik .................................. 623/21 |
| 4,307,473 | * | 12/1981 | Weber ...................................... 623/21 |
| 5,314,485 | * | 5/1994 | Judet ........................................ 623/21 |
| 5,755,804 | * | 5/1998 | Schmotzer et al. ..................... 623/20 |
| 5,766,258 | * | 6/1998 | Simmen .................................. 623/21 |
| 5,782,926 | * | 7/1998 | Lamprecht .............................. 623/21 |

FOREIGN PATENT DOCUMENTS

| | | |
|---|---|---|
| 41398 | 3/1970 | (DE) . |
| 24 45 758 A1 | 4/1975 | (DE) . |
| 27 26 379 A1 | 4/1978 | (DE) . |
| 30 08 292 A1 | 9/1980 | (DE) . |
| 44 06 090 A1 | 8/1995 | (DE) . |
| 44 33 483 C2 | 2/1997 | (DE) . |
| 0 454 646 A1 | 10/1991 | (EP) . |
| 0 532 440 A1 | 3/1993 | (EP) . |

* cited by examiner

*Primary Examiner*—Michael J. Milano
*Assistant Examiner*—Brian Pellegrino
(74) *Attorney, Agent, or Firm*—Alix, Yale & Ristas, LLP (57) ABSTRACT

Wrist prosthesis with a carpus element (2) to be implanted in the metacarpal bones, a radial element (1) to be fixed on the bone of the forearm, and, arranged between these, a transverse axis articulation (3) whose proximal part (9) is connected to the radial element (1). According to the invention, the proximal part (9) of the transverse axis articulation (3) is available in two embodiments, the first of which is rigid per se and the second of which comprises a further articulation (25, 28), and that [sic] both embodiments of the proximal part (9) of the transverse axis articulation (3) are connected or can be connected releasably to the radial element (1) and to the distal part (18) of the transverse axis articulation (3).

13 Claims, 5 Drawing Sheets

HAND JOINT PROSTHESIS

BACKGROUND OF THE INVENTION

The human wrist can execute pivoting movements in all spatial directions, the most important being the pivoting in the dorsal-palmar plane. In a known wrist prosthesis (DE-U 295 00 476), two articulations are therefore provided one behind the other or one within the other, one of them being designed as a transverse axis articulation which is able exclusively to execute a hinge movement for the dorsal-palmar pivoting, the other of them being designed as an elongate socket which is arranged to move essentially transverse to the former. In the case of an unstable ligament apparatus or certain muscle imbalances, prostheses are preferred in which the transverse pivoting is suppressed, with only the transverse axis articulation being provided (DE-U 70 12 087). Hitherto, it has been necessary to decide in each case between different makes, which is difficult when the decision can only be made during surgery.

SUMMARY OF THE INVENTION

The invention is therefore based on the object of making available a prosthesis which allows a decision to be made during surgery.

Accordingly, the proximal part of the transverse axis articulation is connected releasably to the radial element to be anchored in the ulna and is either designed to be rigid per se or is equipped with the further articulation permitting the transverse movement. A prosthesis system is thus obtained which makes it possible to make a decision during surgery as to whether a transverse mobility should be allowed or not and, accordingly, one or other of the alternative embodiments of the proximal part of the transverse axis articulation is used, while the other prosthesis parts remain the same. In particular, this system makes it possible for those elements of the prosthesis to be anchored in the bone to be implanted before a decision has to be taken regarding the transverse mobility of the prosthesis. A subsequent exchange is also made possible by this means.

The connecting arrangements provided between the proximal part of the transverse axis articulation and the radial element are expediently equipped for transmitting force with positive locking. According to a further feature of the invention, these can be pushed into one another essentially in the ulnoradial direction. In this way, a reliable connection is achieved which is independent of any screwing or clamping mechanisms. On the other hand, the said prosthesis part can be inserted without any great distraction between the already implanted carpal and radial elements.

The transverse axis articulation comprises, on one side, a T-type journal and, on the other side, a bearing part which comprises two aligned bores for receiving the T-type journal or its bearing. The T-type journal is pushed into these bores from one end, the outer of these two bores being slotted in the longitudinal direction to allow passage of the central pin of the T-type journal. The insert opening at the end of the bore is then closed. According to the invention, a threaded closure can be provided for this purpose.

The boundary between the mutually releasable distal and proximal parts of the transverse axis articulation can coincide with these bearing surfaces. However, since the bearing functions on the one hand, and the functions relating to the releasability and mutual fixing of the articulation parts, on the other hand, do not necessarily go together, it may be more expedient for all the bearing elements of the transverse axis articulation to be arranged on the distal part.

The carpus element has a plurality of distally extending pegs which are to be inserted into the metacarpal bones and which are connected by a transverse member extending essentially perpendicular to the pegs. It is known to arrange the articulation axis of the transverse axis articulation at an acute angle thereto. According to the invention, this angle is chosen in a range between 0° and 15°, preferably in a narrower range of 5° to 10°.

In the known prosthesis, the socket of the additional universal joint is arranged steeply inclined in relation to the transverse direction. According to the invention, this inclination is reversed in favor of an almost symmetrical design in which the edge tangent, i.e. the connecting line of the edges of the articulation surface of the socket in the palmar plane, encloses an angle of at least 5° and at most 25°, preferably from 10° to 15°, with the radius transverse direction or the complementary angle with the longitudinal direction of a stem to be fixed in the ulna. This angle can be greater in the sagittal plane. The difference between this angle and the angle mentioned in the preceding paragraph gives the directional difference between the carpus element and the radius element, which preferably lies between 0° and 10°. Correspondingly, the angle which the bearing axis encloses with the radius transverse direction, in the rigid version of the proximal part of the transverse axis bearing, is advantageously of the same order of magnitude.

BRIEF DESCRIPTION OF THE DRAWINGS

The invention is explained in greater detail below with reference to the drawing which shows an advantageous illustrative embodiment of the invention, and in which.

DETAILED DESCRIPTION OF THE INVENTION

Figure 1:
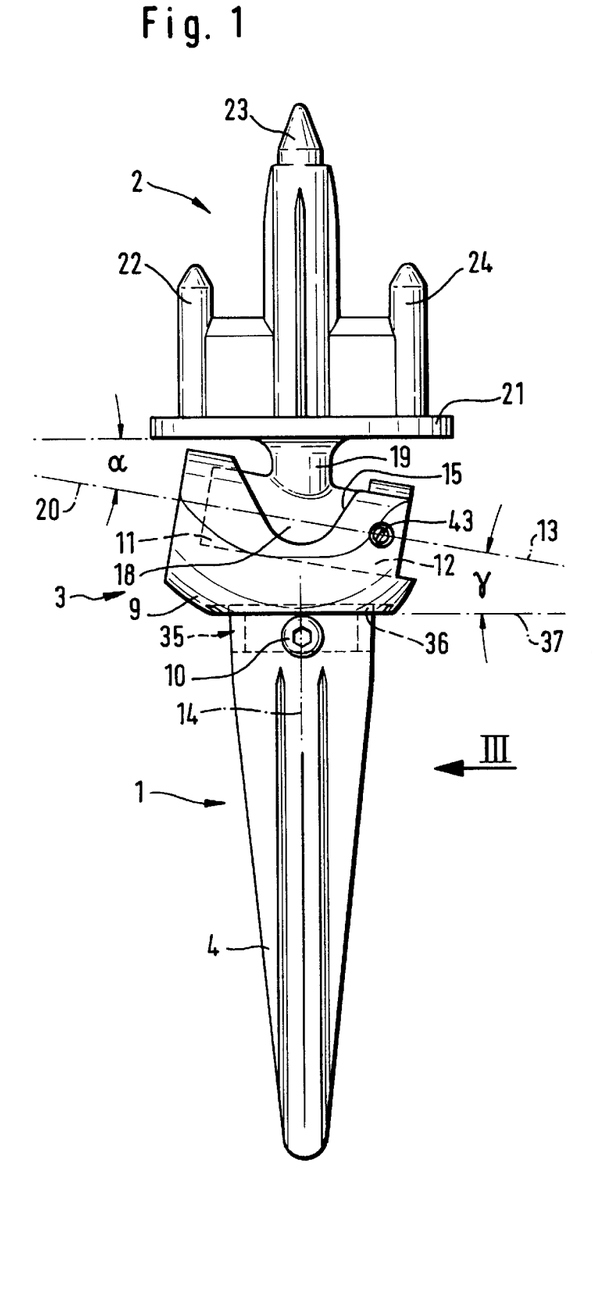
FIGS. 1 and 2 show the dorsal view of a prosthesis according to the invention for the right hand, in both alternative embodiments, at about twice the natural scale.

The prosthesis according to FIG. 1 comprises a radial element 1, a carpus element 2 and a transverse axis articulation 3. The radial element comprises a stem 4 which is to be implanted in the bone cavity at the distal end of the ulna. It ends in a connecting arrangement 35 with ribs and grooves which extend approximately in the ulnoradial direction and which are dovetail-shaped. By means of rib engagement 36 in corresponding grooves of the mating piece, the flanks of the dovetail groove are prevented from escaping from the engaged position in the event of high forces having to be transmitted. After implantation of the stem 4, the proximal part 9 of the transverse axis articulation 3 is capable of being pushed with its connecting arrangement onto that of the stem from the ulnar direction. The positively locking parts of the connecting arrangements provide essentially all of the force transmission. To secure the engagement and the correct relative position, a securing device can be provided, for example a screw 10.

The proximal part 9 of the transverse axis articulation 3 comprises two mutually aligned bore sections 11, 12, the axis 13 of which extends approximately in the ulnoradial direction, i.e. approximately perpendicular to the center axis 14 of the stem 4 in the palmar plane. Situated between the bore sections 11 and 12 there is a cutout 15 which permits up to 70° flexion and extension. The end of the bore section 11 is closed. The outer end of the bore section 12 is initially open. The bore section 12 is slotted at 17 on either side, preferably on the distal side.

The distal part 9 of the transverse axis articulation 3 is formed by a T-type journal 18, 19 whose length and diameter match the bore sections 11, 12 and whose neck piece 19 is pivotable inside the cutout 15 in the assembled state. Details of the embodiments are discussed later with reference to FIG. 8. On assembly, the journal 18 is pushed from the direction of the open side into the bore 11, 12, the neck piece 19 sliding through the slot 17 of the bore section 12. Since the axis 13 and the direction of the ribs and grooves 5 to 8 are approximately parallel, it is possible, after implantation of the carpus element 2 and of the radial element 1 and upon insertion of the proximal part 9 of the transverse axis articulation 3, for the latter to engage simultaneously with the connecting arrangement 35 of the radial element 1 and with the journal 18.

The neck piece 19 of the T-type journal is connected rigidly to a crosspiece 21 of the carpus element 2, from which crosspiece 21 the pegs 22, 23, 24 of the carpus element 2 issue in the distal direction. They lie in a palmar plane and are to be anchored in the metacarpal bones. The crosspiece 21 of the carpus element 2 can be made plate-shaped. Transverse to the palmar plane, its dimensions should be reduced so that it does not obstruct the route of the tendons and nerves.

The axis 20 of the T-type journal 18 extends at an acute angle α to the crosspiece 21 of the carpus element 2. In the example shown, this angle is approximately 10°. The crosspiece 21 extends at 90° to the pegs 22 to 24. The bores 11, 12 in the proximal part of the transverse axis articulation 3 extend, in relation to the transverse direction 37 of the radial element 1, likewise at an angle γ of approximately 10°, so that the longitudinal directions of the pegs 22 to 24 on the one hand and of the stern 4 [sic] on the other hand are aligned with one another or parallel to one another.

It will be readily appreciated that the prosthesis according to FIG. 1 permits a pivoting movement exclusively about the axis 13 of the transverse axis articulation. This prosthesis is therefore suitable particularly in those cases where the natural control of the remaining degrees of freedom of the natural hand by the ligament apparatus and the associated muscles is no longer possible.

Figures 2, 4:
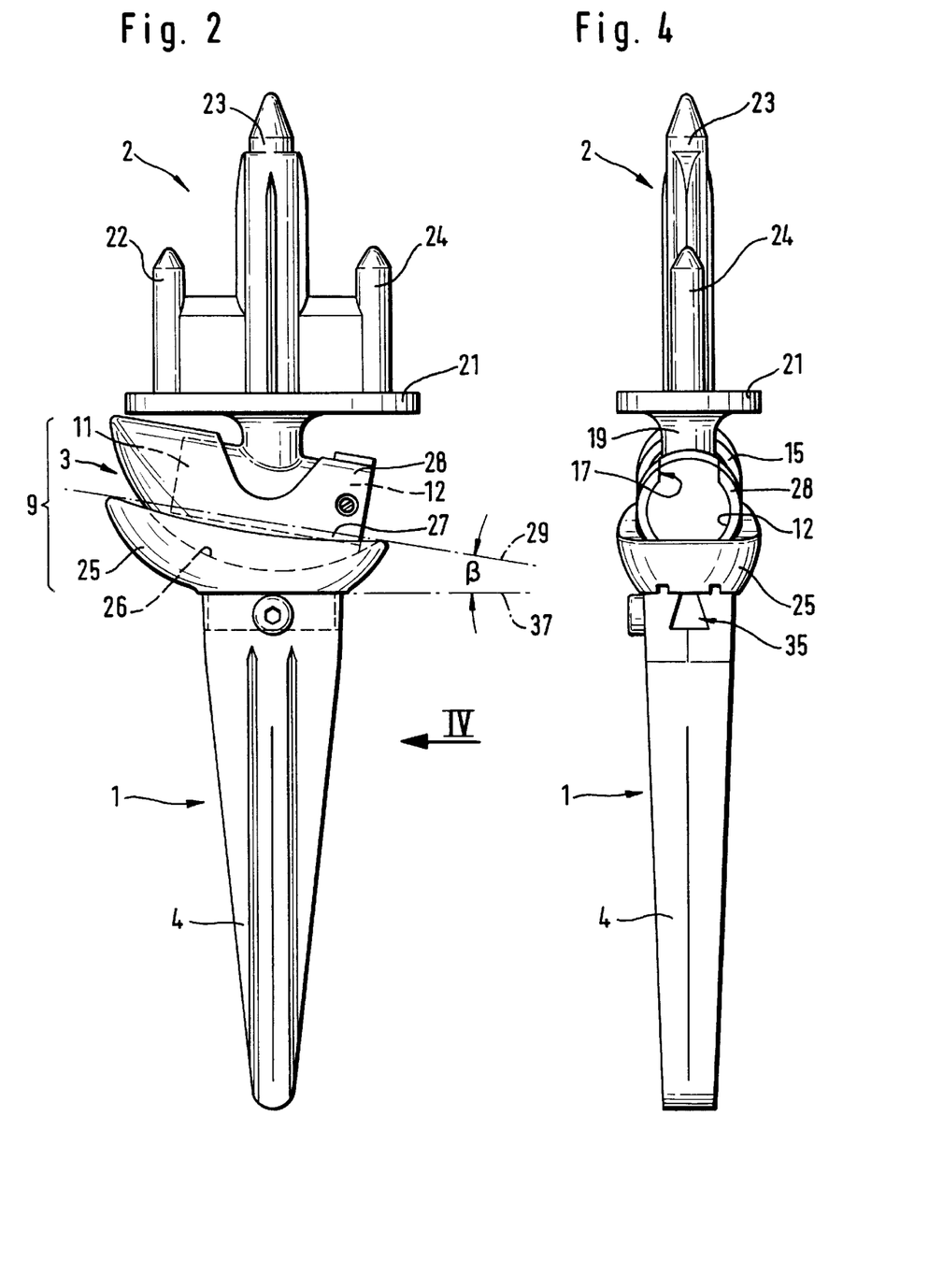
FIGS. 3 and 4 show the corresponding side views in the direction of arrows III and IV, respectively, in FIGS. 1 and 2.
Figure 3:
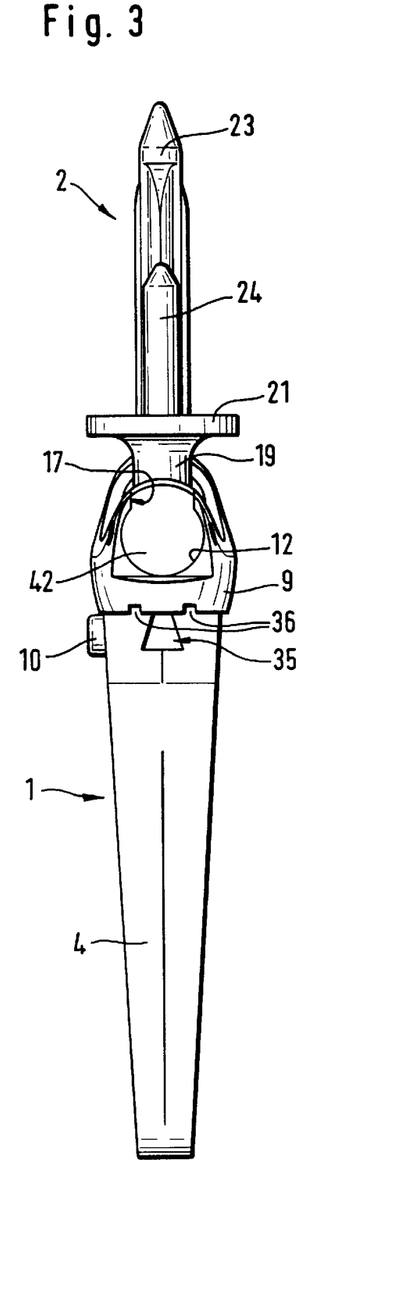
Figures 10, 11:
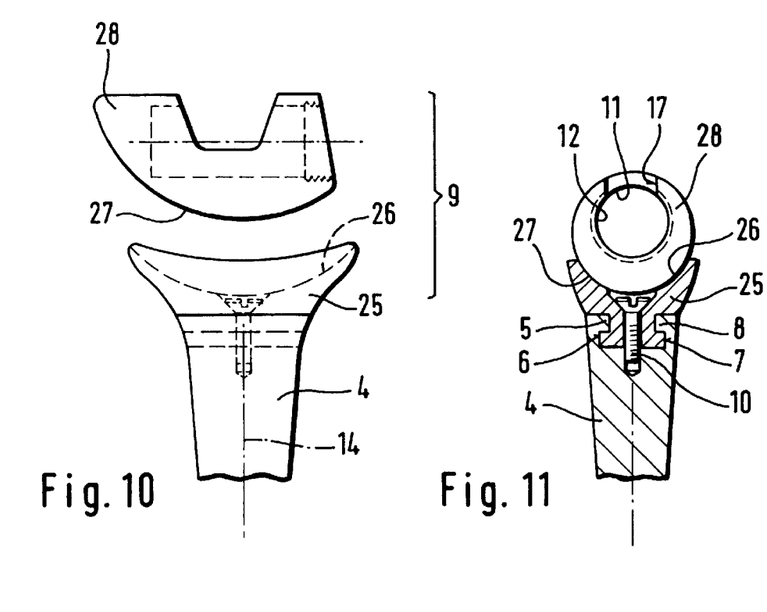

The releasable, rigid connection between the stem 4 and the proximal part 9 of the transverse axis articulation 3 allows this part 9 to be replaced by the part shown at a corresponding position in FIGS. 2 and 4. The embodiment according to FIG. 2 corresponds fully to that according to FIG. 1, except for the presence of a modified proximal part 9 of the transverse axis articulation . The latter is formed by a socket 25 which forms a concave articulation surface 26 pointing in the distal direction, and a complementary convex articulation surface 27, pointing in the proximal direction, on the olive 28 in which the bore sections 11, 12 for the transverse axis bearing are contained. The socket part can be designed so that its height can be varied, e.g. in order to additionally compensate for carpal height reductions as a result of bone defects. The articulation surfaces 26, 27 are preferably not spherical, but elongate in the ulnoradial direction. In the palmar plane (FIG. 2), the radius of curvature and the extension of the articulation surfaces are greater than in the sagittal lane (FIG. 11). The angle β which the edge tangent 29 encloses with the transverse direction of the radial element is about 10° to 15°.

The articulation surfaces 26, 27 permit a pivoting movement (abduction and adduction) in the palmar plane. To ensure that this is possible, their cross-sectional shapes essentially match, viewed in radial planes relative to the common pivot axis. Since the radii of curvature transverse to the palmar plane are essentially smaller than the radius of curvature in the palmar plane, then, in the event of a palmar-dorsal movement (for which the transverse axis articulation is intended), they cannot slide on one another and maintain their full-surface contact and so counteract such a movement. However, they do not act rigidly under this load and therefore permit a certain degree of pronation or supination. Nor are they completely rigid in respect of torsional stress. This satisfies the aim that the prosthesis components should be connected not completely rigidly to one another, in order to relieve the peak forces acting on their anchoring in the bone.

Figure 5:
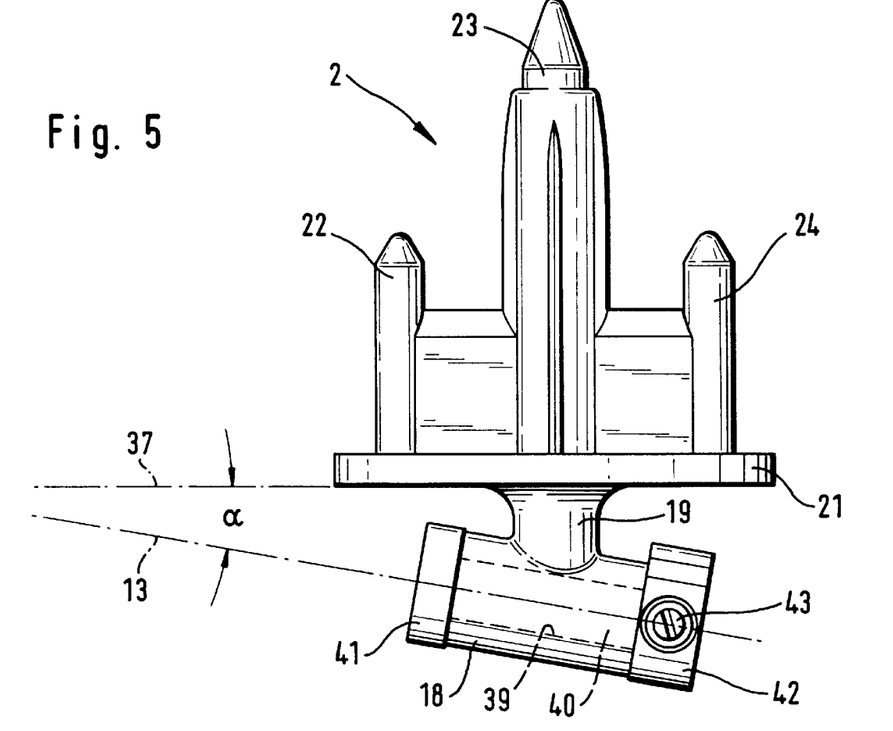
FIG. 5 shows a view, corresponding to FIG. 1, of the carpal element with exposed distal part of the transverse axis articulation.
Figure 6:
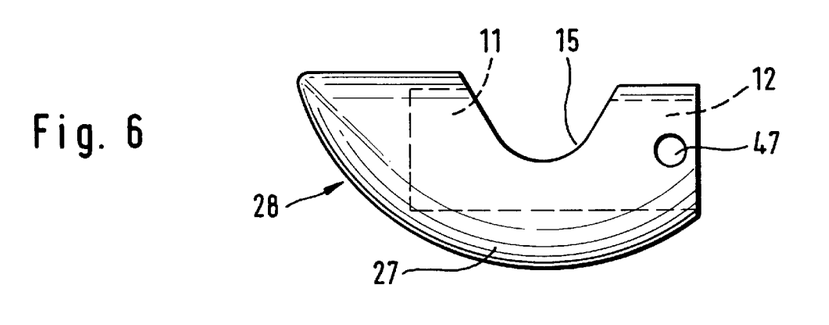
FIGS. 6 and 7 show a side view and a plan view of the olive of the further articulation.
Figure 7:
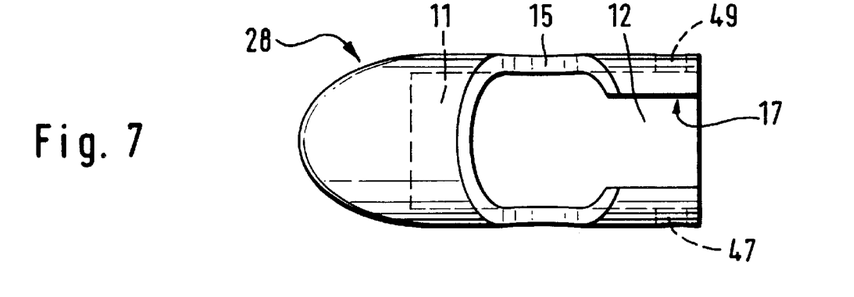
Figure 8:
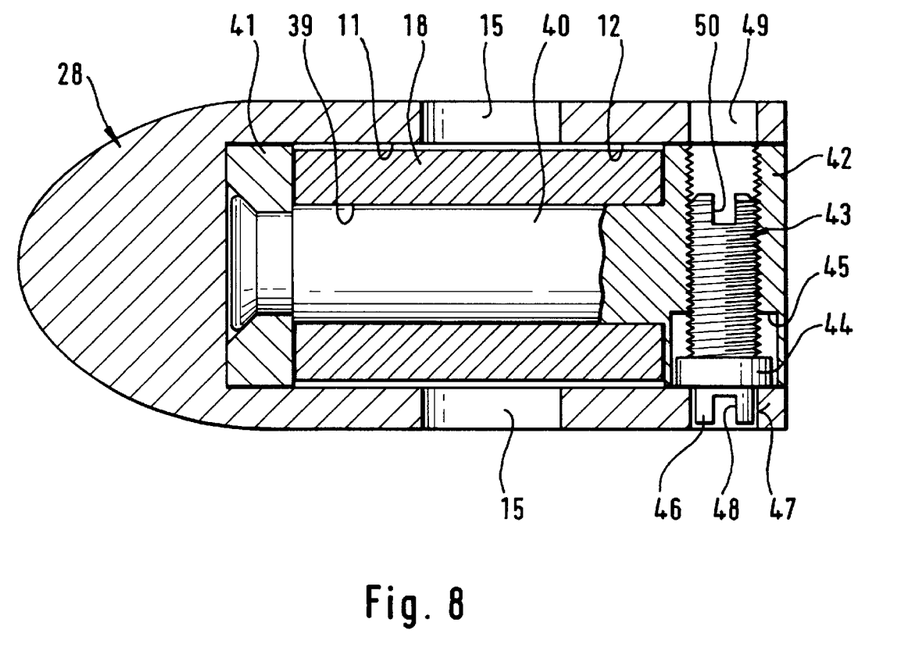
FIG. 8 shows a sectional view of the transverse axis articulation on a larger scale.

As will be seen from FIGS. 5 and 8, the journal 18 of the distal transverse axis articulation comprises a bearing bore 39 which receives a pin 40 which is rigidly connected to two end pieces 41, 42 which are located on each side of the journal 18 and secure the pin 40 therein. The external diameters of the end pieces 41, 42 are a little greater than the external diameter of the journal 18 and are slightly less than the diameter of the bore 11, 12 in the proximal part 9 of the transverse axis bearing. In this embodiment of the prosthesis, the part 18 does not therefore lie on the inner surface of the bore 39, but the end pieces 41, 42. This makes it possible to exempt the bore 11, 12 of the bearing function. The latter is instead taken over by the pin 40 in the bore 39, with the end pieces 41, 42 taking over the axial forces.

To secure the journal 18 and the associated arts in the bore 11, 12, and to transmit the axial forces to the proximal part of the transverse axis articulation, a locking screw 43 is arranged transversely in the end piece 42 (FIG. 8). Its overall length is smaller than the diameter of this end piece 42, so that it does not impede assembly when it is screwed with its collar 44 as far as a corresponding limit stop 45 in the bore contained in the end piece 42. After assembly, it is unscrewed until its head attachment 46 passes into the aligned bore 47 of the olive 28 or of the proximal part 9 of the transverse axis articulation . For this purpose, the head 46 is provided with key surfaces 48 which are accessible via the bore 47 when the prosthesis is used for the right hand. In the case of the left hand being operated on, the opposite side of the prosthesis faces the operating surgeon. Thus, a corresponding bore 49 is provided on the opposite side, this bore 49 giving access to key surfaces 50 provided on the screw base.

Figure 9:
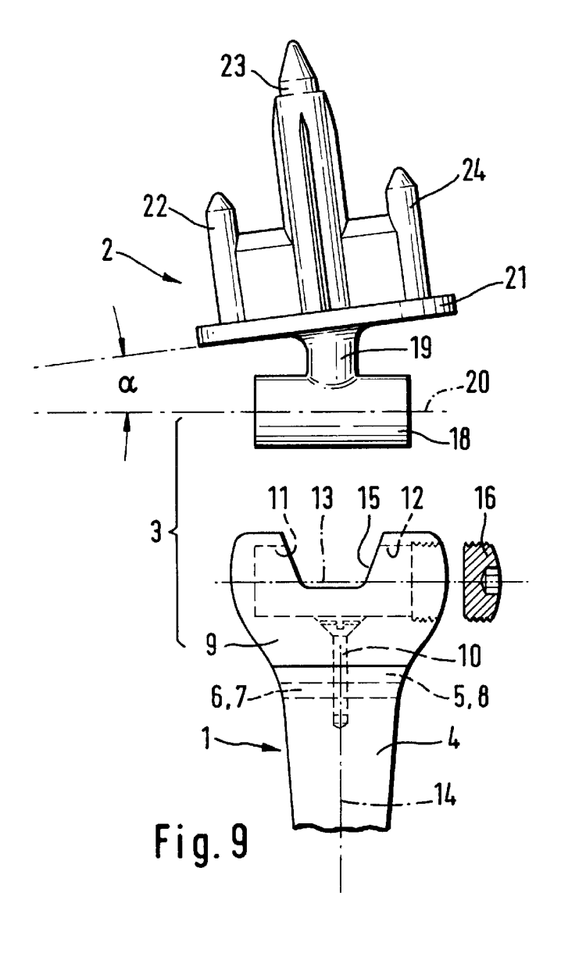
FIGS. 9–11 show corresponding views of a similar illustrative embodiment.

The further illustrative embodiment according to FIGS. 9 to 11 is identical to the above-described embodiment, unless expressly stated otherwise.

The open end of the bore 11, 12 is provided with a thread which permits closure by means of a threaded stopper 16. Instead of this, a snap ring or the like can also be provided.

In the embodiment according to FIG. 9, the axis 13 of the transverse axis articulation is arranged approximately perpendicular to the axis 14 of the radial element. The result of this is that the carpus element with its pegs 22 to 24, on the one hand, and the radial element 4, on the other hand, are set at a slight angle to one another.

Correspondingly, the socket 25, 26 in the embodiment according to FIG. 10 is symmetrical to the axis 14 of the radial element.

For the connecting arrangements between the proximal part 9 of the transverse axis articulation and the radial element 14, an arrangement, differing from the above-described embodiment, of ribs 5, 8 and grooves 6, 7 is provided on the radial element, these cooperating with corresponding ribs and grooves of the proximal transverse axis part.

Finally, a difference between this illustrative embodiment and the one described previously is that the journal 18 of the transverse axis articulation, on the one hand, and the bore 11, 12, on the other hand, directly form the articulation surfaces sliding on one another.

What is claimed is:

1. A multi-configurable wrist joint prosthesis comprising:
   a carpus element to be implanted in the metacarpal bones,
   a radial element including a stem having a first axis, said stem to be implanted in the ulna bone, and
   a transverse axis articulator including a distal part having a second axis, said distal part rigidly connected to said carpus element, said transverse axis articulator further comprising first and second alternatively installable proximal parts which are alternatively releasably installable between said radial element and said distal part when said carpus element is implanted in the metacarpal bones and the stem of said radial element is implanted in the ulna bone,
   each of said first and second proximal parts including a releasable articulation receptacle for receiving said distal part and a releasable connecting arrangement configured to rigidly attach to the stem of said radial element;
   wherein installation of said first proximal part limits articulation of said carpus element to a range of rotation about said second axis and alternate installation of said second proximal part permits articulation of said carpus element in a range of motion about said second axis and a range of pivot relative to said first axis.

2. The wrist joint prosthesis of claim 1, wherein said distal part comprises a T-type journal.

3. The wrist joint prosthesis of claim 2, wherein said T-type journal includes an axial bearing bore, a pin and axially opposed first and second end pieces, said pin is received in said bore and rigidly connected to said end pieces, said pin and bearing bore providing a set of bearing surfaces for supporting rotation of said distal part about said second axis.

4. The wrist joint prosthesis of claim 3, wherein said radial element includes a distal end having a female dovetail connecting arrangement and the connecting arrangement of said first proximal part comprises a male dovetail connecting arrangement complementary to said female dovetail connecting arrangement, said male and female connecting arrangements fitting together to positively lock said first proximal part to said radial element.

5. The wrist joint prosthesis of claim 4, wherein said radial element includes a distal end having female dovetail connecting arrangement and the connecting arrangement of said second proximal part comprises a male dovetail connecting arrangement complementary to said female dovetail connecting arrangement, said male and female connecting arrangements fitting together to positively lock said second proximal part to said radial element.

6. The wrist joint prosthesis of claim 5, wherein said second proximal part comprises:
   a socket including an arcuate elongate concave articulation surface facing in the distal direction, and
   said articulation receptacle comprises an olive-shaped articulation receptacle having an arcuate elongate convex articulation surface facing in the proximal direction and complementary to said socket articulation surface, said olive-shaped articulation receptacle configured to receive said T-type journal, the complementary arcuate elongate articulation surfaces permitting said carpus element a range of pivot relative to said radial element.

7. The wrist joint prosthesis of claim 6, wherein said carpus element comprises a crosspiece and a plurality of pegs rigidly connected to said crosspiece, an angle formed between said second axis and said crosspiece being no greater than 15°.

8. The wrist joint prosthesis of claim 7, wherein said socket comprises an edge tangent which forms an angle of 5° to 25° with a perpendicular to said first axis.

9. The wrist joint prosthesis of claim 8, wherein the articulation receptacle of said first proximal part comprises a bore having two mutually aligned bore sections separated by a cutout, said bore having an open end and a slot connecting said open end to said cutout, said bore being configured to receive said T-type journal from said open end, said open end and said female dovetail connecting arrangement having orientations which permit simultaneous insertion of said T-type journal in said bore and said male dovetail connecting arrangement in said female dovetail connecting arrangement from the same direction.

10. The wrist joint prosthesis of claim 9, wherein said olive-shaped articulation receptacle comprises a bore having two mutually aligned bore sections separated by a cutout, said bore having an open end and a slot connecting said open end to said cutout, said bore being configured to receive said T-type journal from said open end, said open end and said female dovetail connecting arrangement having orientations which permit simultaneous insertion of said T-type journal in said bore and said male dovetail connecting arrangement in said female dovetail connecting arrangement from the same direction.

11. The wrist joint prosthesis of claim 10, wherein a wall surrounds and defines said bore and said open end receives a closure element formed by said second end piece, said closure element includes a locking screw having key surfaces at each axially opposed end, said screw cooperates with a recess in the wall of said bore, and said key surfaces are accessible through said recess and through an opening in said wall axially opposed to said recess.

12. The wrist joint prosthesis of claim 11, wherein a wall surrounds and defines said bore and said open end receives a closure element formed by said second end piece, said closure element includes a locking screw having key surfaces at each axially opposed end, said screw cooperates with a recess in the wall of said bore, and said key surfaces are accessible through said recess and through an opening in said wall axially opposed to said recess.

13. A multi-configuraible wrist joint prosthesis comprising:
   a carpus element to be implanted in the metacarpal bones,
   a radial element including a stem to be implanted in the ulna bone of the forearm, said radial element having a first axis and a distal end including at least one rib and at least one groove which comprise a first connecting arrangement, a transverse axis articulator comprising a distal part including a T-type journal having a second axis, said distal part rigidly connected to said carpus element, said transverse axis articulator comprising a first proximal part including at least one rib and at least one groove which comprise a second connecting arrangement complementary to said first connecting arrangement and two mutually aligned bore sections positioned on either side of a cutout, said bore sections configured to receive said T-type journal, and a second proximal part including a socket which defines an elongate concave articulation surface facing in the distal direction, said socket including at least one rib and at least one groove which comprise a third connecting arrangement complementary to said first connecting arrangement, and an olive-shaped articulation receptacle having an elongate convex articulation surface facing in the proximal direction and two mutually aligned bore sections configured to receive said T-type journal, wherein said first and second proximal parts are alternatively releasably installable between said radial element and said distal part when said carpus element is implanted in the metacarpal bones and the stem of said radial element is implanted in the ulna bone, and installation of said first proximal part limits articulation of said carpus element to a range of rotation about said second axis and alternate installation of said second proximal part permits articulation of said carpus element in a range of motion about said second axis and a range of pivot relative to said first axis.

* * * * *

UNITED STATES PATENT AND TRADEMARK OFFICE
CERTIFICATE OF CORRECTION

PATENT NO.    : 6,168,630 B1
DATED         : January 2, 2001
INVENTOR(S)   : Keller et al.

It is certified that error appears in the above-identified patent and that said Letters Patent is hereby corrected as shown below:

<u>Column 6,</u>
Line 60, change "multi-configuraible" to -- multi-configurable --.

Signed and Sealed this

Twentieth Day of August, 2002

Attest:

Attesting Officer

JAMES E. ROGAN
*Director of the United States Patent and Trademark Office*